(12) United States Patent
Trinh et al.

(10) Patent No.: US 7,784,304 B2
(45) Date of Patent: *Aug. 31, 2010

(54) NON-SLIP ICE BAG DEVICE AND METHOD FOR USING SAME TO TREAT PATIENTS

(76) Inventors: Dennis Sam Trinh, 8671 Creekwood La., Maineville, OH (US) 45039; David Lam Trinh, 8671 Creekwood La., Maineville, OH (US) 45039; Albert Long Trinh, 8671 Creekwood La., Maineville, OH (US) 45039

( * ) Notice: Subject to any disclaimer, the term of this patent is extended or adjusted under 35 U.S.C. 154(b) by 994 days.

This patent is subject to a terminal disclaimer.

(21) Appl. No.: 11/295,898

(22) Filed: Dec. 7, 2005

(65) Prior Publication Data

US 2006/0081000 A1 Apr. 20, 2006

Related U.S. Application Data

(63) Continuation-in-part of application No. 10/455,886, filed on Jun. 6, 2003, now Pat. No. 7,065,983.

(51) Int. Cl.
*F25D 3/08* (2006.01)
(52) U.S. Cl. ...................................... 62/530
(58) Field of Classification Search .............. 62/44, 62/3.62, 259.3, 440, 457, 459, 529, 530; 602/41–60; 156/244.11, 269, 280, 308.4; 604/385.06, 364; 128/402
See application file for complete search history.

(56) References Cited

U.S. PATENT DOCUMENTS

| | | | |
|---|---|---|---|
| 2,403,676 A | | 7/1946 | Modlinski |
| 2,882,692 A | | 4/1959 | Robbins |
| 2,898,744 A | | 8/1959 | Robbins |
| 2,925,719 A | | 2/1960 | Robbins et al. |
| 3,058,313 A | * | 10/1962 | Robbins .................. 62/4 |
| 3,338,284 A | | 8/1967 | Ausnit |
| 3,643,665 A | | 2/1972 | Caillouette |
| 3,780,537 A | * | 12/1973 | Spencer .................. 62/530 |
| 3,885,403 A | * | 5/1975 | Spencer .................. 62/530 |
| 3,893,834 A | * | 7/1975 | Armstrong .............. 62/4 |
| 4,033,354 A | | 7/1977 | De Rosa |
| 4,263,079 A | | 4/1981 | Sutrina et al. |

(Continued)

OTHER PUBLICATIONS

Hotteeze Self-adhesive Heat Pads, p. 1-2 of Notice of Reference—www.sportstek.net/hotteeze.htm.*

*Primary Examiner*—Frantz F. Jules
*Assistant Examiner*—Emmanuel Duke
(74) *Attorney, Agent, or Firm*—Daniel F. Nesbitt; Hasse & Nesbitt LLC (57) ABSTRACT

Non-slip, non-constrictive, self-adhesive ice bag device for use with confined patients that comprises a flexible, preferably water-impermeable outer cover with an open end that is sealable with a leak-proof closure means, said cover having a layer of adhesive to temporarily attach said cover, when it is filled with the cooling medium, or one or more cooling packs containing the cooling medium, to the inside or the outside of a patient-care fabric that is arranged to be in close contact with an injured area of the patient, such that said cooling medium is then in close contact with said injured area, without slippage, and without the need for a potentially constrictive strapping and/or wrapping means.

22 Claims, 4 Drawing Sheets

U.S. PATENT DOCUMENTS

| | | | |
|---|---|---|---|
| 4,363,345 A | 12/1982 | Scheibner | |
| 4,381,025 A * | 4/1983 | Schooley | 607/112 |
| 4,656,697 A | 4/1987 | Näslund | |
| 4,787,754 A * | 11/1988 | Herrington | 383/63 |
| 4,829,641 A | 5/1989 | Williams | |
| 4,887,335 A | 12/1989 | Folkmar | |
| 4,891,501 A * | 1/1990 | Lipton | 607/110 |
| 4,907,321 A | 3/1990 | Williams | |
| 4,958,635 A * | 9/1990 | Roberts | 607/114 |
| 4,967,573 A * | 11/1990 | Wilhelm | 62/530 |
| 4,986,076 A | 1/1991 | Kirk et al. | |
| 5,005,374 A * | 4/1991 | Spitler | 62/259.3 |
| 5,009,828 A | 4/1991 | McCree | |
| D317,571 S | 6/1991 | Henriksson | |
| 5,020,194 A * | 6/1991 | Herrington et al. | 24/400 |
| 5,031,418 A * | 7/1991 | Hirayama et al. | 62/530 |
| 5,069,208 A * | 12/1991 | Noppel et al. | 607/114 |
| 5,070,584 A | 12/1991 | Dais et al. | |
| 5,080,095 A | 1/1992 | Tungate | |
| 5,088,487 A * | 2/1992 | Turner | 607/108 |
| 5,088,971 A * | 2/1992 | Herrington | 493/203 |
| 5,140,727 A | 8/1992 | Dais et al. | |
| 5,148,804 A * | 9/1992 | Hill et al. | 607/108 |
| 5,167,655 A * | 12/1992 | McCoy | 604/396 |
| 5,215,080 A * | 6/1993 | Thomas et al. | 607/112 |
| 5,393,462 A * | 2/1995 | Avery | 516/102 |
| 5,417,790 A * | 5/1995 | Petrou | 156/249 |
| 5,507,794 A * | 4/1996 | Allen | 607/112 |
| D372,674 S | 8/1996 | Weber et al. | |
| 5,545,197 A | 8/1996 | Bowen | |
| D375,045 S | 10/1996 | Weber et al. | |
| 5,598,608 A | 2/1997 | Naslund | |
| 5,647,100 A | 7/1997 | Porchia et al. | |
| 5,697,962 A | 12/1997 | Brink et al. | |
| 5,792,213 A | 8/1998 | Bowen | |
| 5,887,437 A * | 3/1999 | Maxim | 62/4 |
| 5,967,308 A | 10/1999 | Bowen | |
| 5,984,951 A * | 11/1999 | Weiss et al. | 607/109 |
| 6,036,004 A | 3/2000 | Bowen | |
| D423,353 S | 4/2000 | Blanchard et al. | |
| 6,361,553 B1 | 3/2002 | Bowen | |
| 6,362,387 B1 * | 3/2002 | Carson et al. | 602/41 |
| 6,470,705 B2 * | 10/2002 | Bride-Flynn | 62/530 |
| D482,968 S | 12/2003 | Henriksson | |
| 6,681,590 B1 * | 1/2004 | Jones | 62/259.3 |
| 6,886,982 B2 | 5/2005 | Reynolds | |
| 6,904,646 B2 | 6/2005 | Reynolds | |
| 2004/0244413 A1 | 12/2004 | Trinh et al. | |

* cited by examiner

NON-SLIP ICE BAG DEVICE AND METHOD FOR USING SAME TO TREAT PATIENTS

This is a continuation-in-part of U.S. patent application Ser. No. 10/455,886, Albert Long Trinh and David Lam Trinh filed Jun. 6, 2003, now U.S. Pat. No. 7,065,983.

BACKGROUND OF THE INVENTION

1. Field of the Invention

This invention relates to the general field of medical devices and/or methods for cooling an injured area of the body to, e.g., alleviate pain and inflammation, and promote healing. In particular, it relates to a flexible cover for containing ice or a cold pack to form an ice bag that will not slip off the injured area, has improved comfort and convenience, the cover having an adhesive layer on the cover as the attachment means. Thus, it relates to an ice bag cover that has an adhesive means for releasably attaching it to, e.g., a fabric used in the care of a patient, such as a hospital blanket or a hospital gown, to keep the ice bag in close contact with the injured area even when the injured area forms a slope or an inclined or vertical surface, or when the patient changes his or her lying position. It also relates to a method of using such non-slip self-adhering cover for cold treatment. It also relates to an article of manufacture that provides such cover, and to the provision with the cover of instructions for use that help unskilled or uninformed users to provide an effective thermal therapeutic treatment.

2. Description of the Related Art

The desirability of using ice bags for thermal therapy is well accepted. It has long been an accepted medical practice to apply a cooling element to the surface of a body in the vicinity of an injury, e.g., a bone fracture area, a post-surgery area, a bruise or a sprain, to, e.g., reduce swelling, inflammation, and pain. A common ice bag that is commercially available is the reusable type comprising a water-impermeable, commonly a rubber-lined, flexible bag having a tubular rigid neck and a removable cap. To use, the bag is filled with ice cubes or ice chips and closed with the cap, then the bag is applied to the injured area of the body and held in place by hand.

Another type of hand-held cold pack that is commercially available is a refrigeratable gel cold pack which comprises a refrigerant or coolant gel material contained in a plastic housing which can be either flexible or relatively inflexible. The gel packs are stored in a conventional freezer for chilling or cooling and are then ready for use. Also commercially available is an endothermic chemical pack that comprises two or more pouches for separately storing chemical reactants that can be mixed to produce a cooling mixture.

A common home-use ice bag can be made using a commercially available reclosable plastic sandwich and/or freezer bag with a zipper seal, such as a Ziploc™ plastic bag filled with ice (Ziploc is a registered trademark of Dow Chemical Company, Midland, Mich.). By "reclosable" it is meant that the bag can be opened and closed numerous times.

One of the disadvantages of these ice bags is that they need to be inconveniently held by hand to maintain contact with the injured area For a patient who stays still, e.g., in bed, these types of ice bag can be placed on top of the injury without the need for being held in place by hand. However, some injuries occur in the side of the body, that is, the injured area forms a slope or an inclined or vertical surface, or the patient needs to change his or her posture, e.g., from lying on the back to lying on the side, which can cause the ice bag to slide out of place if it is not retained in place by hand.

To overcome this inconvenience, several types of ice bag devices comprising a holder for these ice bags have been created. These ice bag devices can be strapped around a body part, with, e.g., loop and hook mating Velcro™-type fastening straps, such as those disclosed in U.S. Pat. Nos. 5,080,095 issued Jan. 14, 1992 to Tungate; U.S. Pat. No. 5,697,962 issued Dec. 16, 1997 to Brink et al.; U.S. Pat. No. 5,215,080 issued Jun. 1, 1993 to Thomas et al.; and U.S. Pat. No. 5,984,951 issued Nov. 16, 1999 to Weiss et al. U.S. Pat. No. 6,361,553 B1 issued Mar. 26, 2002 to Bowen discloses an ice pack that has attached tie strings to fasten the ice pack to a body part. Since these ice bag devices need to be wrapped and tied around a body part, they are constrictive and can interfere with the blood flow, or otherwise uncomfortable to the wearer, especially to a patient with a serious injury such as post-surgery wound. It can be inconvenient to apply these ice bags to the body and to remove them from the body. The wrapping can also cause pain or discomfort for situations such as bone fracture or post surgery. Furthermore, these ice bag devices are usually of complicated design, large and bulky in size and/or expensive to produce.

U.S. Pat. No. 5,887,437 issued Mar. 30, 1999 to Maxim discloses a cold pack containing sealed water or a chemical cooling mixture that does not have fastening straps, but instead has an extended perimeter with adhesive means to attach the chemical cold pack to a skin surface. However when this self-adhesive chemical cold pack is applied to a skin surface, the removal of the device from the skin surface after use can be uncomfortable, especially when the skin area is close to a surgery.

To overcome the constriction effect of the strapping, there are efforts to develop garments or other devices that can provide the cold therapy without the need to be tightly strapped and/or wrapped. U.S. Pat. No. 2,403,676 issued Jul. 9, 1946 to Modlinski discloses a jacket with a plurality of attached pockets to hold ice packs or ice bags. U.S. Pat. No. 4,891,501 issued Jan. 2, 1990 to Lipton discloses a therapeutic pad, with cooling elements, that can be hung around the neck or the head to treat the muscles of the neck, the chest, the back, and/or the jaw. U.S. Pat. No. 5,167,655 issued Dec. 1, 1992 to McCoy discloses a cold therapy panty provided with a receptacle located adjacent to the crotch area to receive a cold pack for applying cold therapy to the crotch of the wearer. U.S. Pat. No. 4,033,354 issued Jul. 5, 1977 to De Rosa discloses an ice cooling vest-like garment comprising water-filled pockets that are frozen and subsequently attached via Velcro fasteners to the inside of the garment so as to provide body cooling under heat stress conditions. Although these cold pack devices provide an improvement over the prior art, they are of complicated design, large and bulky in size and/or expensive to produce.

Thus, there is a need for an improved, inexpensive and readily available ice bag device that remains in close contact with an injured area of a patient, and eliminates the necessity for holding it by hand or strapping and/or tying it around a body part, even when the injured area forms a slope or an inclined or vertical surface, or when the patient needs to change his or her posture, e.g., from lying on the back to lying on the side, or in a reclining position. There is also a need to keep the ice bag applied to a patient in transit, i.e., being transported from one location to another, when a simple movement of the patient can dislodge an unattached ice bag to the rolling bed or a stretcher, or to the floor. Such ice bag devices can minimize the time the care givers need to spend with the patients. Preferably such ice bag device is easily manufactured and used.

SUMMARY OF THE INVENTION

This invention relates to a non-slip, non-constrictive, self-adhesive ice bag device for use with confined patients, said ice bag device comprising a flexible, preferably water-impermeable outer cover having a sac or pouch structure with dimensions suitable for containing a cold medium, wherein said cover has one open end and a leak-proof closure means, either integral to the sac or pouch structure or provided separately, to seal said open end after said cold medium is added to the inside of said cover, and wherein said cover has one face covered with an adhesive layer to temporarily attach said cover, when it is filled with the cooling medium, or one or more cooling packs containing the cooling medium, to the inside or the outside of a patient-care fabric, e.g., hospital gown, hospital bed sheet, a hospital blanket, or a patient's garment, that is arranged to be in close contact with an injured area of the patient, such that said cooling medium is then in close contact with said injured area, without slippage, and without the need for a strapping means, and wherein said adhesive layer is typically covered with a release layer to avoid premature attachment. The closure means can be an integral part of the outer cover, e.g., when the outer cover is a plastic zipper container or a laminated plastic zipper container which is sealable by an interlocking rib and groove sealing closure. The closure means can also be a separate element such as a bag closure device. In a preferred embodiment, the outer cover is self-adhering with the adhesive layer being an integral part of the outer cover and entirely or partially covering one side of the outer cover. The adhesive layer is optionally but preferably covered with a release paper layer to protect the adhesive from prematurely sticking to a surface other than the intended patient-care fabric surface. In one preferred aspect, the outer cover has one open end to receive a cooling medium which can be ice, ice and water combination, or one or more inner cooling bags or packs, hereinafter simply "pack" or "packs", containing a cooling medium. Each inner cooling pack comprises a sealed, desirably permanently sealed, fluid impermeable plastic container containing a refrigeratable cooling gel, or endothermic chemical cooling mixture, or a leak-proof, reclosable, flexible plastic bag containing ice or an ice and water mixture. The outer cover is preferably liquid-impermeable when it is closed with a leak-proof closure means so that ice can be used. The outer cover can also be liquid-permeable for use with leak-proof inner cooling packs.

This invention also relates to a method for therapeutic cold treatment of injuries by releasably attaching the cover hereinabove which holds a cooling medium to a patient-care fabric so as to apply said cooling medium to an injured area of a patient without slippage and without constriction when the fabric is arranged so that the cooling medium is in close contact with the injured area of the body. In a preferred embodiment it relates to a method of creating a non-slip and non-constrictive ice bag device using said outer cover by filling said outer cover with ice or ice and water mixture, or by inserting a cooling pack in said outer cover, via the open end, sealing the open end with the closure means, and using the adhesive layer to attach the assembled ice bag device to the inside or the outside of a patient-care fabric, such that said ice bag device is in close contact with said injured area, without slippage, and without the need for a strapping and/or wrapping means.

The present invention also relates to the association of instructions for use with the non-slip and non-constrictive ice bag device disclosed hereinabove, or with the method using said device, to ensure that the method can be practiced efficiently, quickly, and effectively so as to maximize the effect of the cooling treatment on an injury.

The present invention also relates to an article of manufacture comprising the flexible outer cover hereinabove, with a closure means which can be either an integral interlocking rib and groove sealing closure or a separate bag-closure device, optionally, one or more resealable or permanently sealed liquid impermeable containers disclosed hereinabove, optionally, a sealed plastic wrapper to keep the outer cover and the optional elements in a hygienic, non-contaminated condition in storage, and optionally packaged in association with instructions for use comprising an instruction to direct the consumer to attach the assembled ice bag device to the inside or the outside of a patient-care fabric.

The present invention also relates to a method of using an adhesive means to reversibly attach an ice bag device to a patient-care fabric and cover such fabric on the body of the patient such that said ice bag device is in close contact with an injured body part of said patient, wherein said ice bag device comprises a flexible outer cover containing an inner container filled with a cooling medium.

Other non-limiting alternative embodiments of the non-slip self-adhesive ice bag device of the present invention are illustrated in FIG. 1 to FIG. 22 of U.S. patent application Ser. Nos. 10/455,886, which are shown with brief descriptions as paragraphs [0017] to [0038] on pages 2 and 3 of U.S. Pat. Appl. Pub. No. US 2004/0244413 A1 Dec. 9, 2004, said Patent Application and Patent Application Publication being incorporated herein by reference.

DETAILED DESCRIPTION OF THE INVENTION

In one aspect of this invention there is provided a non-slip, non-constrictive, self-adhesive ice bag device comprising a flexible, preferably liquid impermeable cover having dimensions suitable for containing a cold medium and having a layer of mounting adhesive for use to temporarily attach said outer cover to the inside or the outside of a patient-care fabric, e.g., hospital gown, hospital bed sheet, a hospital blanket, or a patient's garment, that is arranged to be in close contact with the injured area of a patient, such that said cold medium is then in close contact with said injured area, without slippage, and without a need for a strapping or wrapping means, while allowing people taking care of the patient to replace the cooling medium without changing the placement of the device or excessively disturbing the patient, and wherein said cover has a sac or pouch structure with three closed sides and one open side, or end, and has a leak-proof closure means to seal the open side after the cold medium is added to the inside of the cover, and wherein said cover is made of a relatively flexible substrate, preferably a laminated substrate. The outer leak-proof closure protects the patient-care fabrics from liquid to avoid the need for replacing the patient-care fabric and thus disturbing the patient.

In a preferred embodiment, the outer cover is self-adhering with the adhesive layer being an integral part of the outer cover and entirely or partially covering one side of the outer cover. The adhesive layer is preferably hypoallergenic. The adhesive layer is optionally but preferably covered with a release layer, e.g., release paper, to protect the adhesive from prematurely sticking to a surface other than the intended fabric while the cover is stored before use or is being handled or positioned for use. Optionally, the release sheet can be composed of several pieces instead of one whole sheet, with or without fold(s), to allow easy removal.

In one preferred aspect, the cover is liquid impermeable and has one open end to receive a cooling medium which can be ice, ice and water combination, or one or more inner leak-proof cooling bags or packs, hereinafter simply "pack" or "packs", containing a cooling medium. Each inner cooling pack comprises either a permanently sealed fluid impermeable plastic container containing a refrigeratable cooling gel, or endothermic chemical cooling mixture, or a resealable, e.g., by an interlocking rib and groove sealing closure, plastic container containing ice or a water and ice mixture. For easy replacement, the cooling medium is itself sealed to make handling easier.

The outer cover is preferably liquid-impermeable when it is closed with a leak-proof closure means so that ice can be used. The outer cover can also be liquid-permeable for use with leak-proof inner cooling packs. In a preferred embodiment, the wall of the cover is preferably made of laminated materials such as laminates of plastic and woven or non-woven fabric layers, with the inner plastic layer providing the liquid impermeability and the optional construction of the zipper closure and the outer fabric layer providing a degree of insulation to slow the cooling of the treated body part, to avoid damage by overcooling, e.g., frostbite.

"Leak-proof closure means", as used herein, means a mechanism or an element of the outer cover or a device that closes the open end of the liquid impermeable outer cover of the present invention such that any liquid, water or melted ice, that is contained in the interior of the cover cannot escape or seep to the outside of the cover. However, it is also desirable to use sealed inner packs to make replacement easier and to minimize any chance for the patient-care fabrics, or patient, getting wet.

"Patient-care fabric", as used herein, means a piece of fabric or garment, such as, but not limited to, a hospital gown, a hospital bed sheet, a hospital blanket, or a patient's garment, and the like, that is wrapped to cover, or worn to cover a part of the body of, e.g., a patient in a hospital or a care center or an infirmary, convalescence home, a nursing home, or an injured person confined in a bed at home. The advantages of using an adhesive rather than a tie are many. A tie can become constrictive and replacing the tie can require moving the patient. The adhesive can be placed using the adhesive so as not to constrict and the placement can be changed by moving the patient-care fabric.

The flexible outer cover is preferably a unitary structure, typically a sac structure (or pouch structure) with one open end to receive a cooling medium, and preferably said open end can be closed with a closure means. The closure means can be an integral part of the outer cover, e.g., when the outer cover is a plastic zipper container or a laminated plastic zipper container which is sealable by an interlocking rib and groove sealing closure. The closure means can also be a separate element such as a bag-closure device. The preferred closure device that is useful for the ice bag device of the present invention is that with a clamping mechanism. Non-limiting examples of such closure device are disclosed in, e.g., U.S. Pat. Nos. 6,886,982 B2 issued May 3, 2005 and U.S. Pat. No. 6,904,646 B2 issued Jun. 14, 2005, both to Reynolds; U.S. Pat. Nos. 5,598,608 issued Feb. 4, 1997 to Naslund; and U.S. Pat. No. 4,887,335 issued Dec. 19, 1989 to Folkmar, all said patents are incorporated herein by reference. The suitable closure device that is useful in the non-slip, self-adhesive ice bag device of the present invention includes those disclosed in these U.S. patents after they are adapted and adjusted for the size, the dimensions, and the thickness of the ice bag device of the present invention such that any liquid, water or melted ice, that is contained in the interior of the cover cannot escape or seep to the outside of the cover.

The outer cover can have any suitable shape such as rectangular, square, oval, and the like. Preferably the flexible outer cover has a generally rectangular or square configuration when flattened to facilitate storage and to more efficiently contain ice or typical inner cooling packs.

Figure 6:
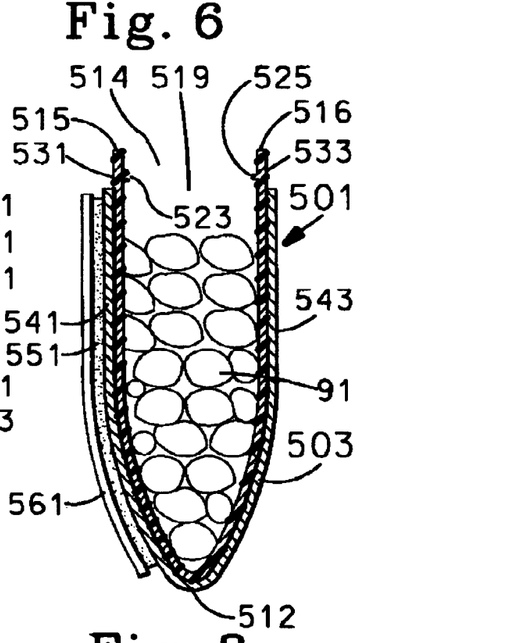
FIG. 6 is a cross-sectional view of the ice bag device of FIG. 5 taken along the line 6-6.
Figure 7:
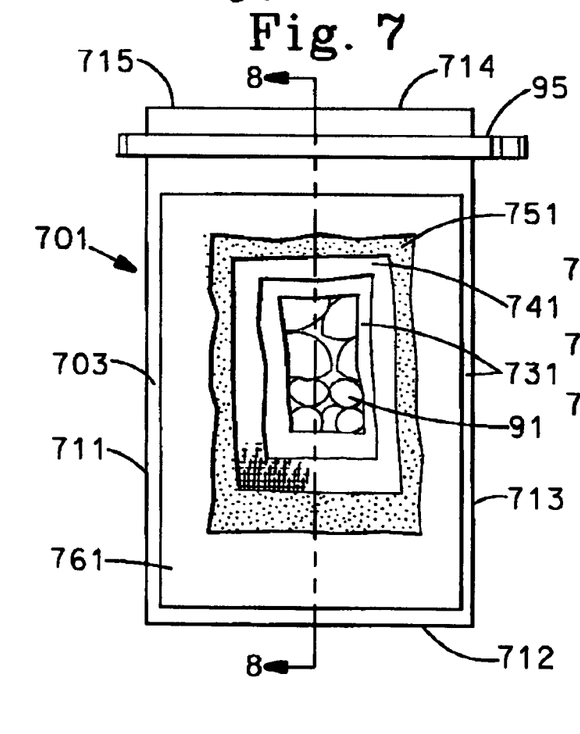
FIG. 7 is a perspective view of an alternative embodiment of the non-slip ice bag device of the present invention, comprising a flexible liquid impermeable cover with a sac structure having three closed sides and one open side, and with one face covered with a mounting adhesive layer, wherein the flexible liquid-impermeable cover is formed by laminated material, and wherein the open side is closed by a leak-proof bag clip closing device to retain the ice chips, said cover being partly cut away to show said ice.
Figure 8:
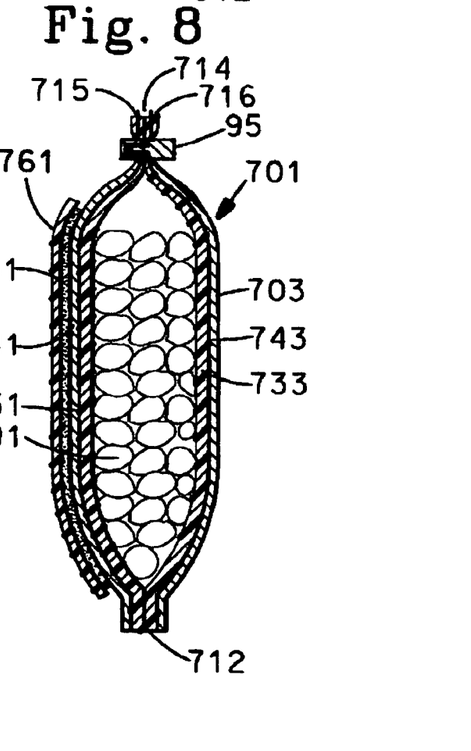
FIG. 8 is a cross-sectional view of the ice bag device of FIG. 7 taken along the line 8-8.

The mounting adhesive layer can either practically cover one entire face of the outer cover as is depicted in FIGS. 1 and 5 of U.S. patent application Ser. No. 10/455,886, or cover only part of that face, preferably as adhesive strips that cover one or more edges of the outer cover, more preferably two adhesive strips that cover two opposite edges, as are depicted in FIG. 6 and FIG. 7, or one or more adhesive strips that cover all four edges of the outer cover, as are depicted in FIG. 8, all of U.S. patent application Ser. No. 10/455,886. Optionally, the adhesive strips may be placed in parallel extending continuously from one edge to the opposing edge, or optionally the adhesive strips are in the form of of intermittent strands. The adhesive strips preferably have a suitable width to keep the ice bag device securely attached to the patient-care fabric. Typically the adhesive strips have a width of at least about 0.5 cm, preferably at least about 1 cm, and more preferably at least about 1.5 cm.

Figure 9:
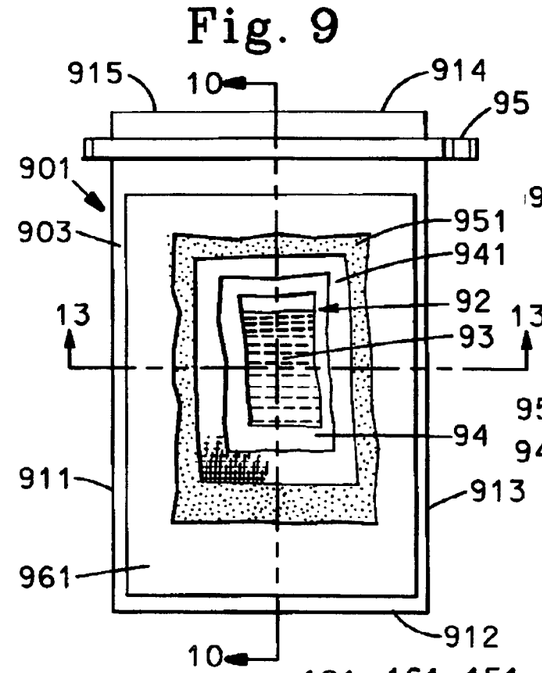
FIG. 9 is a perspective view of an alternative embodiment of the non-slip ice bag device of the present invention, comprising a flexible liquid impermeable cover with a sac structure having three closed sides and one open side, and with one face covered with a mounting adhesive layer, wherein the flexible liquid-impermeable cover is formed by laminated material, and wherein the open side is closed by a clip closing device to retain a cooling gel pack, said cover being partly cut away to show said gel pack.
Figure 12:
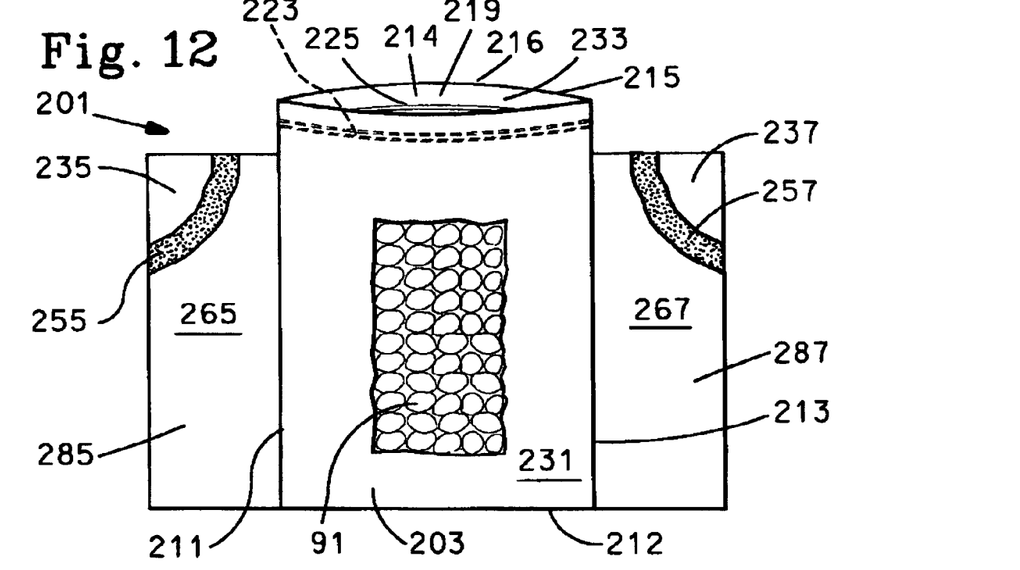
FIG. 12 is a perspective view of an alternative embodiment of the non-slip ice bag device of the present invention, in an open configuration, comprising a flexible liquid impermeable cover with a sac structure having three closed sides and one open side and two extended peripheries covered with mounting adhesive, wherein the open side is sealable by a leak-proof zipper closure to retain ice.
Figure 14:
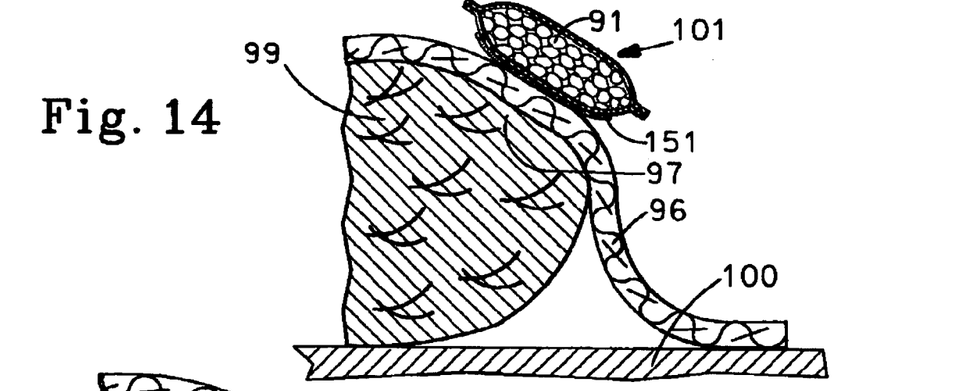
FIG. 14 is a cross sectional view of the ice bag device 101 of FIG. 11 (and FIG. 1) being attached to the outside of a patient-care blanket which is arranged such that said ice bag device is in close contact with the injured area in an inclined position of a patient.

In a preferred embodiment, the outer cover has two or more extended peripheries (or extended edges) that are extensions from the edges of the outer cover, and are covered with a mounting adhesive layer for use to attach the outer cover to the patient-care fabric, in addition to or instead of the adhesive layer on the body of the outer cover, as are depicted in FIG. 9, FIG. 12, and FIG. 14 of U.S. patent application Ser. No. 10/455,886. Each extended periphery along each edge can have a length that is shorter, equal or longer than the corresponding edge. The periphery extension typically has a width of at least about 1 cm, preferably at least about 1.5 cm, more preferably at least about 2 cm, and less than about 20 cm, preferably less than about 8 cm, and more preferably less than about 6 cm.

An advantage of the ice bag device of the current invention is its non-slip property that keeps the device in close contact with an injured area of a patient, without the necessity for holding it by hand or strapping and/or tying it around a body part, even when the injured area forms a slope or an inclined or vertical surface, or when the patient needs to change his or her posture, e.g., from lying on the back to lying on the side. Thus the need for the ice bag device to be tied around a body part is avoided, since such tying, being constrictive, can interfere with the blood flow, or otherwise be uncomfortable to the wearer. Therefore, the non-slip, non-constrictive ice bag device of the present invention is preferably without attached tie strings.

The outer cover is made at least partly of a relatively flexible substrate. In a preferred embodiment, the substrate is either a leak-proof, water-impermeable plastic layer, such as a polyethylene film or polypropylene film, or more preferably a laminated substrate such as a laminate of plastic and woven, film coated nonwovens, or non-woven fabric layers comprising an inner plastic (such as polyethylene) layer providing the liquid impermeability and the optional construction of the zipper closure and the outer insulating layer providing a degree of insulation to slow the cooling of the treated body part, to avoid damage by overcooling, e.g., frostbite. A suitable degree of insulation is desirable for bedridden patients who may not be able to adjust or remove the ice bag device when it becomes excessively cold or uncomfortable, and to keep the temperature in the therapeutic range. The insulating substrate layer is typically a non-woven, woven, and/or knitted fabric, but can also be a resilient foam sheet. A closed-cell resilient foam sheet can replace the leak-proof laminate substrate. The outer cover can also be liquid-permeable for use with leak-proof inner cooling packs. The outer insulating layer and the substrate for the liquid permeable outer cover can be made of material such as, but not limited to, woven, knitted, crocheted, or non-woven fabric of natural and/or synthetic fibers such as cotton, polyester, nylon, acrylic, rayon, and the like, felt, velvet, flocked material, heat-bonded plastic fiber material, such as, melt-blown, spun-bonded polyethylene or polypropylene, carded thermo-bonded polypropylene and rayon blend, solvent-laid thermally bonded polypropylene (e.g., Tyvek™ by Dupont), resilient open-cell or close-cell plastic foam sheet, porous and nonporous plastic film and/or rubber, paper, laminated materials such as laminate of rubber and non-woven layers, and the like. Both sides of the device can be insulated to avoid heat flow into the device from the environment.

The edges of the outer cover can be sealed by sewing, gluing, heat sealing, or the like, or can be integral or continuous, e.g., when formed from tubular material that requires no sealing on the side edges, or from the fold of the two faces resulting in the bottom edge that is opposite from the open side. The preferred material makes the outer cover of the ice bag device flexible, conformable, and optionally stretchable, at least on the side that is in contact with the body. The material that contacts the body also preferably slows the cooling of the body part to avoid damage by overcooling, e.g., frostbite. The material should allow heat to flow from the injured body part. Preferably, the material does not allow heat to flow through it at a rate that will result in frostbite. The desired effect is cooling without freezing and the cooling is preferably at a rate that creates no more pain than can be withstood by the user and which does not cause damage to the treated area.

Figure 5:
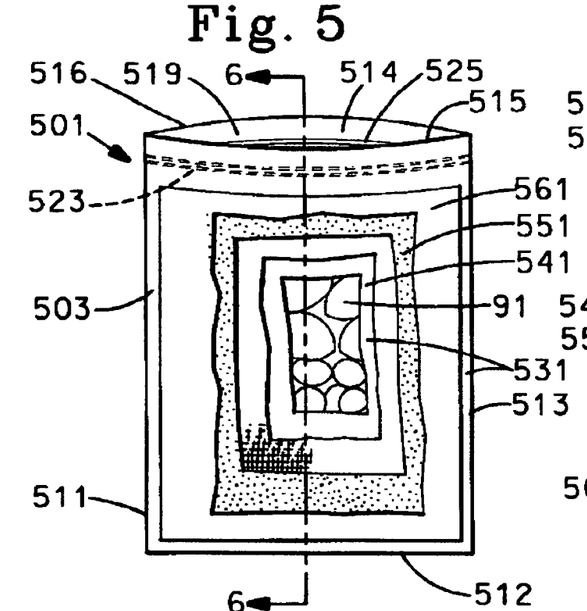
FIG. 5 is a perspective view of an alternative embodiment of the non-slip ice bag device of the present invention, wherein the flexible liquid-impermeable cover is formed by laminated material.
Figure 11:
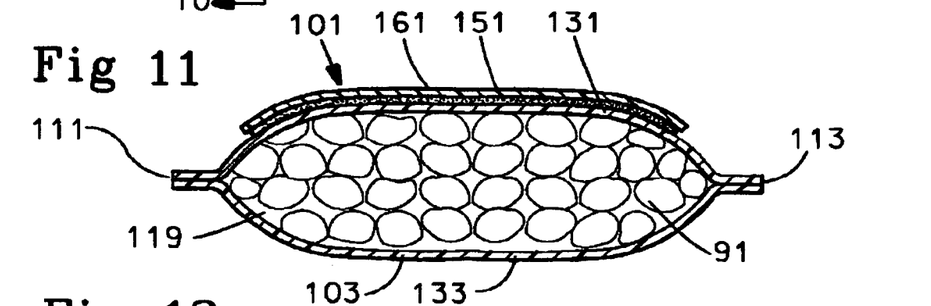
FIG. 11 is a cross-sectional view of the ice bag device of FIG. 1 taken along the line 11-11.

Typically the outer cover has two faces or sides that join together at the edges to form a sac or pouch structure having one open end and three closed edges. The edges of the outer cover can be sealed by sewing, gluing, heat sealing, or the like, or can be integral, e.g., when formed from tubular material that requires no sealing on the side edges. Typically the two faces or sides of the outer cover have about the same dimensions and form a more or less flat sac or pouch. In a preferred embodiment, the two faces or sides of the outer cover have different dimensions, with the face coated with the adhesive layer and/or strips having a narrower size, and the face without the adhesive being wider. The two faces join together at the closed edges with the narrower face taking a more or less flat configuration, while the wider face taking a protruding or bulging configuration to form one or more bulging interior compartments to contain one or more inner cooling packs, as is illustrated in FIG. 5, FIG. 11, and FIG. 17 of U.S. patent application Ser. No. 10/455,886. The flat configuration of the face coated with adhesive improves the adhesion of the ice bag device to the garment surface.

The outer cover can most conveniently have one compartment designed to have dimensions suitable to hold ice chips or ice and water mixture, or alternatively it can hold one inner cold pack comprising an at least relatively liquid impermeable inner container containing a cooling medium. The inner cooling pack can be inserted into the compartment through the open end of the outer cover. The inner cooling pack is preferably composed of a resealable or permanently sealed plastic liquid impermeable inner container to contain a cooling medium, wherein said cooling medium is preferably either ice, ice and water combination, water, refrigeratable cooling gel, or endothermic chemical cooling system. Ice, and ice and water mixture are preferably contained in a resealable or reclosable plastic container, such as a reclosable zipper bag, which is conveniently either a commercially available reclosable zipper bag such as a sandwich or freezer zipper bag, as described hereinafter, or a specially made zipper bag of any suitable size and thickness. The use of a reclosable bag allows one to replace the cooling medium when it is no longer cool. A refrigeratable cooling gel and/or an endothermic chemical cooling system is preferably contained in permanently sealed plastic containers. Non-limiting examples of inner cold packs useful for the non-slip ice bag device of the present invention are given in paragraphs [0066] to [0071] on pages 6 and 7 of U.S. patent application Ser. No. 10/455,886.

Another aspect of this invention relates to a non-slip, non-constrictive, self-adhesive ice bag device that can be attached to a patient-care fabric for use with confined patients, said ice bag device comprising a flexible, water-impermeable outer cover having a leak-proof closure means and having one face covered at least partially with an adhesive layer as described hereinabove, wherein the outer cover contains ice cubes, ice chips, crushed ice, or ice and water mixture.

This invention also relates to a method for therapeutic cold treatment of injuries by releasably attaching the liquid impermeable cover hereinabove which holds a cold medium to a patient-care fabric so as to apply said cold medium to an injured area of a patient without slippage and without constriction when the fabric is arranged so that the cooling medium is in close contact with the injured area of the body. In a preferred embodiment it relates to a method of creating a non-slip and non-constrictive ice bag device using said outer cover by filling said outer cover with ice or ice and water mixture, or by inserting a cooling pack in said outer cover, via the open end, sealing the open end with the leak-proof closure means, and using the adhesive layer to attach the assembled ice bag device to the inside or the outside of a patient-care fabric, preferably to the inside of the patient-care fabric, such that said ice bag device is in close contact with said injured area, without slippage, and without the need for a potentially constrictive strapping and/or wrapping means. Attaching the device to the inside of the patient-care fabric places the insulated layer that is on the side opposite the adhesive layer, against the patient's body. Placing the device on the outside of the patient-care fabric has the advantage that the personnel providing patient care can reach the device, e.g., to replace the cooling medium or reposition the device without disturbing the patient and/or without using too much time. Outside placement also permits a visual check on the device from a distance. Accordingly, it is desirable for the device to have some kind of temperature indicator, or to be transparent, so that the personnel providing patient care can determine the need for cooling medium replacement without disturbing the patient.

There are situations wherein the weight of the cold medium in the ice bag device of this invention is too heavy, or the weight of the patient-care fabric is too light, such that when the ice bag is on a slanted or vertical surface, the weight of the cold medium may tend to pull the patient-care fabric down. Therefore, the present invention also relates to a method for keeping the patient-care fabric and thus the ice bag device in place, by tucking a part of the patient-care fabric that is on the opposite side of the ice bag device in relation to the body of the patient under a bedding element such as a mattress, or under the patient's body, or having a means such as Velcro to keep the patient-care fabric in place.

The present invention also relates to a method of using an adhesive means to reversibly attach an ice bag device to a patient-care fabric and place such fabric on the body of the patient so that said ice bag device is in close contact with an injured body part of said patient, wherein said ice bag device comprises a flexible outer cover being a sac structure with one open end, having one face covered with a mounting adhesive layer, and having dimensions to form one or more compartments suitable for containing one or more cooling packs, wherein each cold pack comprises one inner, generally liquid impermeable, container containing a cooling medium, said cover being disclosed fully in U.S. patent application Ser. No. 10/455,886.

The present invention also relates to an article of manufacture comprising the flexible outer cover as described hereinabove, with a closure means which can be either an integral interlocking rib and groove sealing closure or a separate bag-closure device, and optionally at least one other element which is: one or more empty reclosable relatively liquid-impermeable plastic containers, or sealed, liquid impermeable plastic containers containing a cooling medium such as water, refrigeratable cooling gel, or endothermic chemical system, preferably one or more empty reclosable zipper containers, to contain a cooling medium, that can fit inside the enclosure of the outer cover, and optionally, a sealed plastic wrapper to keep the outer cover and the optional elements in a hygienic, non-contaminated condition in storage, and optionally packaged in association with instructions for use comprising an instruction to direct the consumer to attach the assembled ice bag device to the inside or the outside of a patient-care fabric using an adhesive attachment means.

The present invention also relates to the association of instructions for use with the non-slip and non-constrictive ice bag device disclosed hereinabove, or with the method using said device, to ensure that the method can be practiced efficiently, quickly, and effectively so as to maximize the effect of the cooling treatment on an injury and/or to minimize patient discomfort and patient care personnel time. Said set of instructions can instruct a user how to use the cover to assemble the non-slip ice bag device, and/or how to use the product properly, and/or to ensure that the user knows what benefits can be achieved, and/or how best to obtain these benefits, wherein the instructions are in one or more languages, and wherein the instructions are in words or words in combination with illustrative images and/or icons. Said set of instructions can instruct a user to tuck a part of the patient-care fabric that is on the opposite side of the ice bag device in relation to the body of the patient under a bedding element such as a mattress, or under the patient's body for keeping the ice bag device in place.

Figure 1:
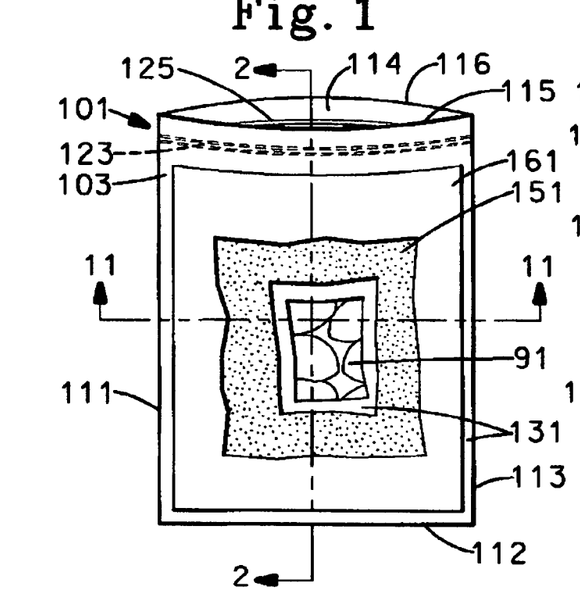
FIG. 1 is a perspective view of a non-slip, non-constrictive, self-adhesive ice bag device of the present invention, in an open configuration, comprising a flexible liquid impermeable cover with a sac structure having three closed sides and one open side, and with one face covered with a mounting adhesive layer, wherein the open side is sealable by a leak-proof zipper closure to retain ice chips, said cover being partly cut away to show said ice.
Figure 2:
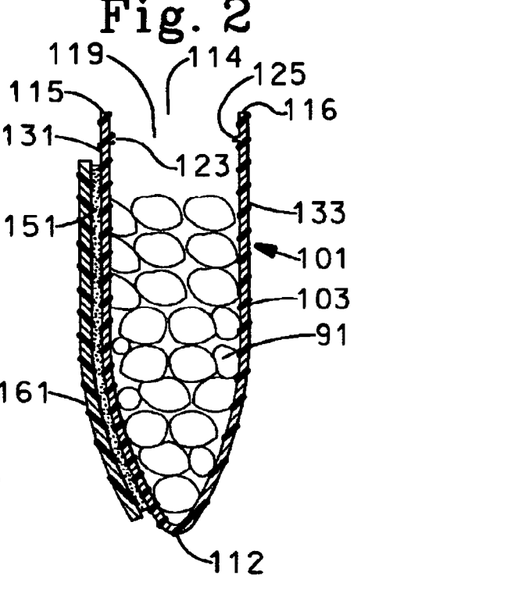
FIG. 2 is a cross-sectional view of the ice bag device of FIG. 1 taken along the line 2-2.
Figure 3:
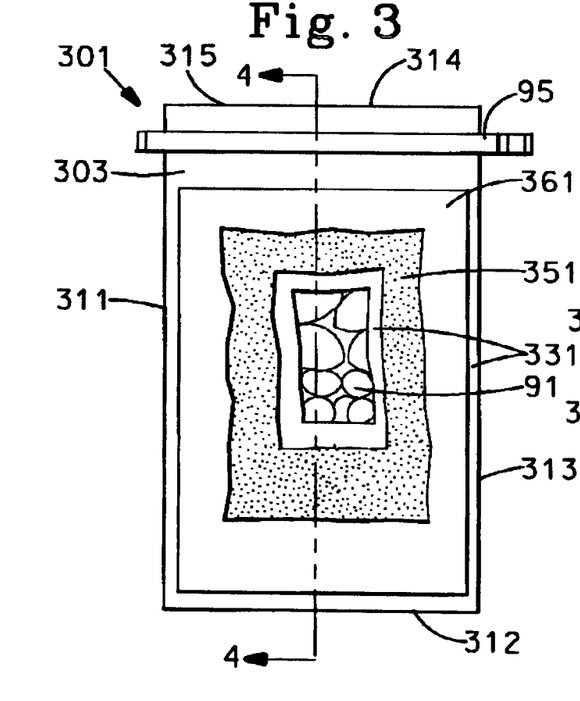
FIG. 3 is a perspective view of an alternative embodiment of the non-slip ice bag device of the present invention, comprising a flexible liquid impermeable cover with a sac structure having three closed sides and one open side, and with one face covered with a mounting adhesive layer, wherein the open side is closed by a leak-proof bag clip closing device to retain the ice chips, said cover being partly cut away to show said ice.
Figure 4:
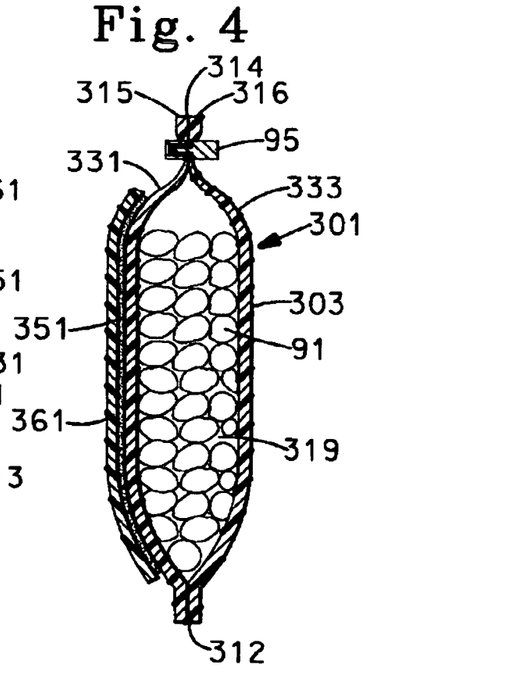
FIG. 4 is a cross-sectional view of the ice bag device of FIG. 3 taken along the line 4-4.

Specific embodiments are described hereinafter with reference to the drawings:

FIGS. 1, 2, and 11 are three views of a non-slip, non-constrictive, self-adhesive, water-impermeable ice bag device of the present invention, in an open configuration, designated as 101 and comprising the flexible outer cover 103. FIG. 1 is a plan view of the outer cover with a portion of the cover being partly cut away to show the ice chips 91 contained inside. FIG. 2 is a cross-sectional view of the ice bag device 101 taken along the line 2-2 of FIG. 1. FIG. 11 is a cross-sectional view of the ice bag device 101 taken along the line 11-11 of FIG. 1. The outer cover 103 has a sac structure having flexible side 131 and side 133 which are made of, e.g., a flexible plastic, such as polyethylene. The two faces of the outer cover 103 are joined along the periphery on three sides to form three closed edges 111, 112, and 113, and an open end 114 comprising two edges 115 and 116, which together define the cover interior 119. In this particular 101 device, edges 111 and 113 are sealed edges, while edge 112 is a fold line. The two flexible side 131 and side 133 are provided with a pair of sealing strips 123 (female) and 125 (male) which are parallel and close to the top edges 115 and 116 to form a leak-proof zipper closure means. A layer of mounting adhesive 151 is positioned on top and substantially covers the whole surface of face 131. Release paper sheet 161 covers the adhesive layer 151 to protect the adhesive from prematurely sticking to a surface other than the intended patient-care fabric. In use, the release paper 161 is removed to expose the adhesive layer 151 to affix the ice bag device 101 comprising the outer cover 103 containing the ice 91 to the surface of a patient-care fabric at a location that is in close contact with the injured area of a patient, as shown in FIG. 14. FIG. 1 also shows the outer cover 103 partly cut away to show ice chips 91. The cut away also shows part of the underlying face 131, and part of the adhesive layer 151. This embodiment allows the use of the device on the outside of the patient-care fabric while the side of the device nearest the patient has an insulating quality FIGS. 3 and 4 are two views of an alternative embodiment of the non-slip, non-constrictive, self-adhesive, water-impermeable ice bag device of the present invention, designated as 301 and comprising the flexible outer cover 303. FIG. 3 is a plan view of the outer cover with a portion of the cover being partly cut away to show the ice chips 91 contained inside. FIG. 4 is a cross-sectional view of the ice bag device 301 taken along the line 13-13 of FIG. 3. The outer cover 303 has a sac structure having flexible side 331 and side 333 made of, e.g., a flexible plastic, such as polyethylene. The two sides 331 and side 333 of the outer cover 303 are joined along the periphery on three sides to form three closed edges 311, 312, and 313, and an open end 314 comprising two edges 315 and 316. Edges 311, 312 and 313 are sealed edges. A layer of mounting adhesive 351 is positioned on top and substantially covers the whole surface of side 331. Release paper sheet 361 covers the adhesive layer 351 to protect the adhesive. The open end 314 is closed by a leak-proof bag-clip closing device 95 to retain the ice chips. FIG. 3 also shows the outer cover 303 partly cut away to show ice chips 91. The cut away also shows part of the underlying side 331, and part of the adhesive layer 351.

FIGS. 5 and 6 are two views of an alternative embodiment of a non-slip, non-constrictive, self-adhesive, water-impermeable ice bag device of the present invention, in an open configuration, designated as 501 and comprising the flexible outer cover 503. FIG. 5 is a plan view of the outer cover with a portion of the cover being partly cut away to show the ice chips 91 contained inside. FIG. 6 is a cross-sectional view of the ice bag device 501 taken along the line 6-6 of FIG. 5. The outer cover 503 has a sac structure having flexible sides comprising of flexible, e.g., plastic, such as polyethylene, layers 531 and 533 laminated with substrate layers 541 and 543. The two sides 531 and 533 of the outer cover 503 are joined along the periphery on three sides to form three closed edges 511, 512, and 513, and an open end 514 with two edges 515 and 516, which together define the cover interior 519, and with edge 512 being a fold line. The two flexible side 531 and side 533 are provided with a pair of sealing strips 523 (female) and 525 (male) which are parallel and close to the top edges 515 and 516 to form a leak-proof zipper closure means. A layer of mounting adhesive 551 is positioned on top and substantially covers the whole surface of face 541. Release paper sheet 561 covers the adhesive layer 551 to protect the adhesive from prematurely sticking to a surface other than the intended patient-care fabric. In use, the release paper 561 is removed to expose the adhesive layer 551. FIG. 5 also shows the outer cover 503 partly cut away to show ice chips 91. The cut away also shows part of the underlying face 531, part of the substrate layer 541, and part of the adhesive layer 551.

FIGS. 7 and 8 are two views of an alternative embodiment of the non-slip, non-constrictive, self-adhesive, water-impermeable ice bag device of the present invention, designated as 701 and comprising the flexible outer cover 703. FIG. 7 is a plan view of the outer cover with a portion of the cover being partly cut away to show the ice chips 91 contained inside. FIG. 8 is a cross-sectional view of the ice bag device 701 taken along the line 8-8 of FIG. 7. The outer cover 703 has a sac structure having flexible sides comprising of flexible, e.g., plastic, such as polyethylene, layers 731 and 733 laminated with substrate layers 741 and 743. The two sides 731 and side 733 of the outer cover 703 are joined along the periphery on three sides to form three closed edges 711, 712, and 713, and an open end 714 comprising two edges 715 and 716. A layer of mounting adhesive 751 is positioned on top and substantially covers the surface of side 741. Release paper sheet 761 covers the adhesive layer 751 to protect the adhesive. The open end 714 is closed by a leak-proof bag-clip closing device 95 to retain the ice chips. FIG. 7 also shows the outer cover 703 partly cut away to show ice chips 91. The cut away also shows part of the underlying side 731, part of the substrate layer 741, and part of the adhesive layer 751.

Figure 10:
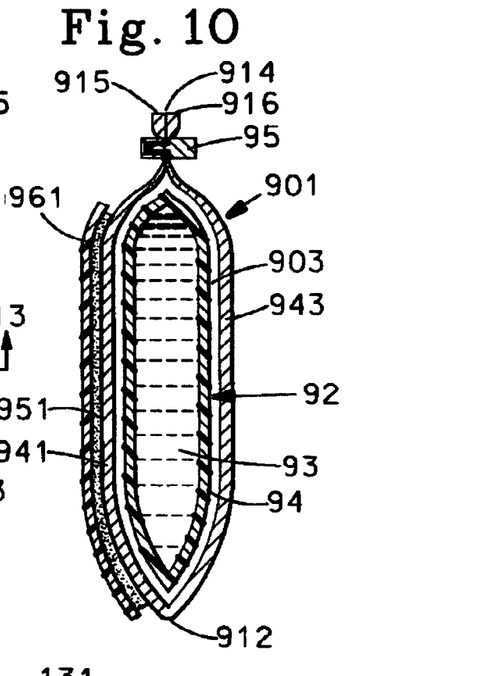
FIG. 10 is a cross-sectional view of the ice bag device of FIG. 9 taken along the line 10-10.
Figure 13:
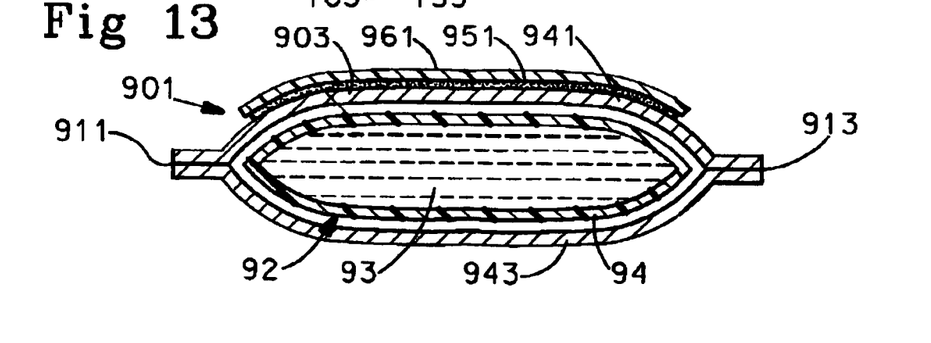
FIG. 13 is a cross-sectional view of the ice bag device of FIG. 9 taken along the line 13-13.

FIGS. 9, 10, and 13 are three views of an alternative embodiment of the non-slip, non-constrictive, self-adhesive ice bag device of the present invention, designated as 901 and comprising the flexible outer cover 903. FIG. 9 is a plan view of the ice bag device 901. FIG. 10 is a cross-sectional view of the ice bag device 901 taken along the line 10-10 of FIG. 9. FIG. 13 is a cross-sectional view of the ice bag device 901 taken along the line 13-13 of FIG. 9. The outer cover 903 has a sac structure having flexible sides comprising flexible substrate layers 941 and 943 which can be either water permeable or water-impermeable. The two sides 941 and side 943 of the outer cover 903 are joined along the periphery on three sides to form three closed edges 911, 912, and 913, and an open end 914 comprising two edges 915 and 916. In this particular 901 device, edges 911 and 913 are sealed edges, while edge 912 is a fold line. A layer of mounting adhesive 951 is positioned on top and covers the surface of side 941. Release paper sheet 961 substantially covers the adhesive layer 951 to protect the adhesive. The open end 914 is closed by a bag-clip closing device 95 to retain the ice chips. FIG. 9 also shows the outer cover 903 partly cut away to show the refrigeratable cooling gel pack 92 which comprises cooling gel 93 contained in a permanently sealed plastic container 94. The cut away also shows part of the substrate layer 941, and part of the adhesive layer 951. The cooling gel pack 92 can be replaced either by an endothermic chemical cooling system or a resealable plastic zipper container containing ice, or an ice and water combination.

FIG. 12 is a perspective view of an alternative embodiment of the non-slip, non-constrictive, self-adhesive, water-impermeable ice bag device of the present invention, in an open configuration, designated as 201 and comprising the flexible outer cover 203. The outer cover 103 has a sac structure having flexible side 231 and side 233 which are made of, e.g., a flexible plastic, such as polyethylene, and are joined along the periphery on three sides to form three closed edges 211, 212, and 213, and an open end 214 comprising two edges 215 and 216, which together define the cover interior 219. The two flexible sides 231 and 233 are provided with a pair of sealing strips 223 (female) and 225 (male) which are parallel and close to the top edges 215 and 216 to form a leak-proof zipper closure means. The cover 203 has two extended peripheries 235 and 237 that are extensions from the closed edges 211 and 213 and are covered with adhesive strips 255 and 257, respectively. In turn, the adhesive strips 255 and 257 are covered with the release paper strips 265 and 267. In use, the release paper strips 265 and 267 are removed to expose the adhesive strips 255 and 257 to affix the ice bag device 201 to the surface of a patient-care fabric at a location that is in close contact with the injured area of a patient. FIG. 12 shows portions of the outer cover 203 partly cut away to show the ice chips 91 contained inside, and part of the underlying extended peripheries 235 and 237, and part of the adhesive strips 255 and 257.

FIG. 14 is a cross sectional view of ice bag device 101 taken along the line 11-11 (as given in FIG. 11) being attached to the outside of patient-care blanket 96 by means of the adhesive layer 151, wherein the ice bag device 101 which contains ice chips 91 is arranged such a manner that said ice bag device is in close contact with the injured area 97 in an inclined position of patient 99 who is laying on bed 100.

Figure 15:
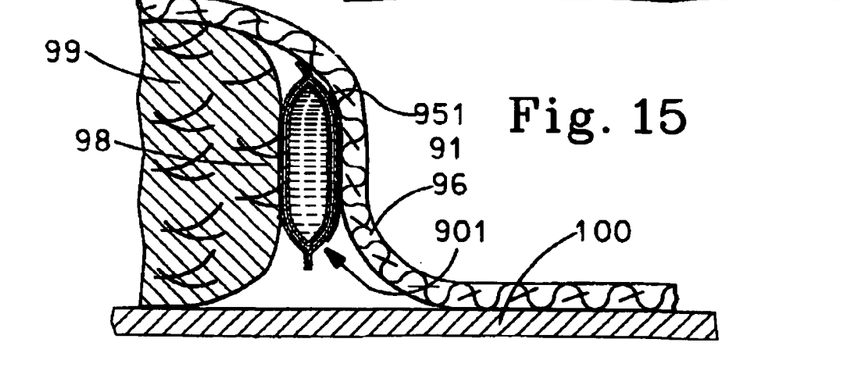
FIG. 15 is a cross sectional view of the ice bag device 901 of FIG. 13 (and FIG. 9) being attached to the inside of a patient-care blanket which is arranged such that said ice bag device is in close contact with the injured area in a vertical position of a patient.

FIG. 15 is a cross sectional view of ice bag device 901 taken along the line 13-13 (as given in FIG. 13) being attached to the inside of patient-care blanket 96 by means of the adhesive layer 951, wherein the ice bag device 901 which contains ice chips 91 is arranged such a manner that said ice bag device is in close contact with the injured area 98 in a vertical position of a patient 99 who is laying on bed 100.

The above description discloses, by way of example, some preferred embodiments of the present invention. However, persons of ordinary skill in the art are capable of creating numerous modifications within the scope of the claims. Changes in specifics of form and details can be made to the above-described embodiments. The claims and not the examples are the measure of the protected invention.

What is claimed is:

1. A self-adhesive ice bag device comprising a flexible outer cover being a sac structure having dimensions suitable for containing a cold medium, wherein the cover has one open end and a leak-proof, recloseable means to seal said open end after the cold medium is added to the inside of the outer cover, wherein said cover comprises relatively flexible, liquid impermeable walls to contain either ice chips or ice and water mixture or an inner cold pack that is either a permanently sealed fluid impermeable plastic container containing a refrigeratable cooling gel or an endothermic chemical cooling mixture, liquid impermeable plastic layer, a closed cell foam layer, or a laminated layer comprising a plastic layer and a substrate layer, and wherein said cover has at least one mounting adhesive layer that can be used to temporarily attach said cover to the inside or the outside of a patient-care fabric that is arranged to be in close contact with the injured area of a patient, such that said cooling medium is then in close contact with said injured area, without slippage, and without a need for a strapping means around said patient, and wherein said adhesive is covered with a release layer.

2. The ice bag device of claim 1 wherein said cover has a generally rectangular or square configuration when flattened.

3. The ice bag device of claim 1 wherein said adhesive layer can either cover one entire face of the outer cover or cover only part of that face as said outer cover with one or more adhesive strips.

4. The ice bag device of claim 3 wherein said adhesive strips cover one or more edges of the outer cover.

5. The ice bag device of claim 3 wherein each said adhesive strip has a width of at least about 1 cm.

6. The ice bag device of claim 2 wherein said cover has 1 or more extended peripheries from the edges of said outer cover, wherein each extended periphery is covered with a mounting adhesive layer that can be used to temporarily attach said outer cover to said patient-care fabric, in addition to or instead of the adhesive layer on the face of the outer cover, and wherein each said adhesive layer is covered with the release layer.

7. The ice bag device of claim 1 wherein said plastic layer is a polyethylene film or polypropylene film.

8. The ice bag device of claim 1 wherein said laminated layer comprises a plastic layer and a substrate layer to provide a degree of insulation to avoid excessive cooling and frostbite, said substrate layer being either woven, knitted, crocheted, non-woven fabric of natural and/or synthetic fibers, felt, velvet, flocked material, heat-bonded plastic fiber material, solvent-laid thermally bonded plastic fiber material, open-cell plastic foam, close-cell plastic foam, porous plastic film, nonporous plastic film, rubber, and/or paper.

9. The ice bag device of claim 1 wherein said cover comprises relatively flexible walls formed from materials that are either woven, knitted, crocheted, non-woven fabric of natural or synthetic fibers, felt, velvet, flocked material, heat-bonded plastic fiber material, solvent-laid thermally bonded plastic fiber material, open-cell plastic foam, close-cell plastic foam, porous plastic film, nonporous plastic film, rubber, paper, or combinations of such materials, and wherein the cold medium is one of: a permanently sealed fluid impermeable plastic container containing a refrigeratable cooling gel, an endothermic chemical cooling mixture, or a leak-proof, flexible plastic zipper bag container containing ice or an ice and water mixture.

10. The ice bag device of claim 1 wherein said outer cover is a plastic zipper container or a laminated plastic zipper container which is sealable by an interlocking rib and groove sealing closure.

11. The ice bag device of claim 1 wherein said closure means is a separate bag-closure device.

12. The ice bag device of claim 11 wherein said separate bag-closure device comprises a clamping mechanism.

13. The ice bag device of claim 1 comprising a flexible, water-impermeable outer cover containing ice cubes, ice chips, crushed ice, or ice and water mixture and having a leak-proof closure means selected from an interlocking rib and groove sealing closure or separate bag-closure device.

14. The ice bag device of claim 1 wherein the patient-care fabric is selected from the group consisting of a hospital gown, a hospital bed sheet, and a hospital blanket.

15. An article of manufacture comprising the following elements: one or more outer covers being flexible sac structures, each having one open end and having dimensions suitable for containing a cold medium, and each comprising at least one mounting adhesive layer; one or more liquid impermeable outer covers and an equal number of separate bag-closure devices, if the covers do not comprise leak-proof closures, optionally one or more separate leak-proof clip closure means to seal open end after the cold medium is added to the inside of the outer cover; one or more cold medium selected from the group consisting of empty zipper bag containers, one or more refrigeratable gel cold packs, and one or more endothermic chemical cold packs; optionally a seal plastic film wrapper to contain one or more of said elements; and optionally, packaged in association with said elements, a set of instructions that tells a user how to use the outer cover to assemble an ice bag device, and/or how to use the product properly, and/or to ensure that the user knows what benefits can be achieved, and/or how best to obtain these benefits, wherein the instructions are in one or more languages, and wherein the instructions are in words or words in combination with illustrative images and/or icons.

16. The article of claim 15, wherein said set of instructions include an instruction telling the user to tuck a part of a patient-care fabric that is on the opposite side of the ice bag device in relation to the body of the patient under a bedding element, or under the patient's body for keeping the ice bag device in place.

17. The article of claim 15 comprising one or more outer covers and one refrigeratable gel pack.

18. A method for therapeutic cold treatment of injuries using an ice bag device providing a self-adhesive ice bag device containing a cold medium, the ice bag device comprising a flexible outer cover having one open end at least one mounting adhesive layer, and being a sac structure having dimensions suitable for containing the cold medium, wherein said cover is liquid impermeable, and said cold medium comprises ice selected from the group consisting of ice cubes, ice chips and crushed ice, and a mixture of such ice and water, and a release layer covering the adhesive layer, removing the release paper from the adhesive layer, and attaching temporarily and releasably said outer cover containing the cold medium to the inside or the outside of a patient-care fabric selected from the group consisting of a hospital gown, a hospital bed sheet, and a hospital blanket that is arranged to be in close contact with the injured area of a patient, such that said cold medium is then applied to said injured area, without slippage, and without a need for a separate strapping means.

19. The method of claim 18 wherein said outer cover is attached to the inside of the patient-care fabric.

20. The method of claim 18 wherein said cold medium is one of: a permanently sealed fluid impermeable plastic container containing a refrigeratable cooling gel or an endothermic chemical cooling mixture, or a leak-proof, reclosable, flexible plastic zipper bag container containing ice or an ice and water mixture.

21. The method of claim 18 wherein a part of said patient-care fabric that is on the opposite side of said ice bag device in relation to the body of the patient is tucked under a bedding element, or under the patient's body.

22. A method for therapeutic cold treatment of injuries using an ice bag device, comprising the steps of:
1) providing an ice bag device containing one or more cold packs, the ice bag device comprising a flexible outer cover being a sac structure with one open end, having dimensions to form one or more compartments suitable for containing the one or more cold packs, and having one face covered with a mounting adhesive layer, and where each cold pack comprises one inner, generally liquid impermeable, container containing a cooling medium;
2) temporarily and releasably attaching said ice bag device to the inside or the outside of a patient-care fabric; and
placing said patient-care fabric on the body of the patient such that said ice bag device is in close contact with an injured body part of said patient.

* * * * *